(12) United States Patent
Martini et al.

(10) Patent No.: US 9,345,801 B2
(45) Date of Patent: May 24, 2016

(54) APPARATUS AND METHOD OF CLEANING GAS IN BLOW MOULDING MACHINES

(75) Inventors: Oliver Martini, Konolfingen (CH); Juergen Soellner, Beratzhausen (DE); Ulrich Lappe, Regensburg (DE); Michael Dahmen, Hamburg (DE); Eduard Handschuh, Regensburg (DE); Michael Neubauer, Regensburg (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 13/110,738

(22) Filed: May 18, 2011

(65) Prior Publication Data
US 2011/0286899 A1 Nov. 24, 2011

(30) Foreign Application Priority Data

May 20, 2010 (DE) .......................... 10 2010 022 129

(51) Int. Cl.
*A61L 9/00* (2006.01)
*A61L 9/16* (2006.01)
*B01D 46/00* (2006.01)
*A61L 2/00* (2006.01)
*A61L 2/18* (2006.01)
(Continued)

(52) U.S. Cl.
CPC ................. *A61L 9/16* (2013.01); *B01D 46/002* (2013.01); *B01D 46/0012* (2013.01); *B01D 46/0023* (2013.01); *B29C 49/46* (2013.01); *A61L 9/04* (2013.01); *A61L 2209/14* (2013.01); *A61L 2209/211* (2013.01); *B01D 53/8671* (2013.01); *B01D 2257/91* (2013.01); *B01D 2279/65* (2013.01); *B29C 49/06* (2013.01); *B29C 49/12* (2013.01); *B29C 49/36* (2013.01); *B29C 49/4284* (2013.01); *B29C 2049/4635* (2013.01); *B29C 2049/4697* (2013.01); *Y02P 70/267* (2015.11)

(58) Field of Classification Search
CPC ........... A61L 9/04; A61L 9/015; A61L 2/002; A61L 9/16; B01D 46/0012; B01D 46/002; B01D 46/0023; B29C 49/46
USPC ............................ 422/4, 5, 120, 122, 28, 292
See application file for complete search history.

(56) References Cited

U.S. PATENT DOCUMENTS 3,650,678 A   3/1972   Hansen .............................. 21/91
3,783,157 A *   1/1974   Frank ............................ 264/528
(Continued)

FOREIGN PATENT DOCUMENTS

CN   2273646   2/1998   .............. B29C 49/28
DE   1781495   1/1959
(Continued)

OTHER PUBLICATIONS

German Office Action, dated Feb. 8, 2012 (4 pgs).
(Continued)

*Primary Examiner* — Regina M Yoo
(74) *Attorney, Agent, or Firm* — Hayes Soloway P.C.

(57) ABSTRACT

An apparatus and method are described for cleaning gas in blow moulding machines for shaping plastics material preforms to form plastics material containers. The apparatus includes at least one gas-processing device, which is capable of filtering the gas in a sterile manner and/or of reducing a quantity of an oxidative disinfecting/sterilizing agent contained in the gas flowing through and/or flowing past, is arranged in at least one gas line which is a gas supply line or a gas removal line of a blowing station.

13 Claims, 4 Drawing Sheets

(51) Int. Cl.
    *A62B 7/08*     (2006.01)
    *A61L 9/04*     (2006.01)
    *B01D 53/86*    (2006.01)
    *B29C 49/42*    (2006.01)
    *B29C 49/46*    (2006.01)
    *B29C 49/06*    (2006.01)
    *B29C 49/12*    (2006.01)
    *B29C 49/36*    (2006.01)

(56) References Cited

U.S. PATENT DOCUMENTS

| | | | |
|---|---|---|---|
| 4,714,647 A * | 12/1987 | Shipp et al. | 428/212 |
| 4,880,581 A * | 11/1989 | Dastoli et al. | 264/39 |
| 5,759,218 A | 6/1998 | Martin et al. | |
| 6,119,433 A | 9/2000 | Kitahora et al. | |
| 6,159,421 A * | 12/2000 | Fujii | 422/4 |
| 7,128,872 B2 * | 10/2006 | Robitaille et al. | 422/28 |
| 7,157,046 B2 * | 1/2007 | McVey et al. | 422/28 |
| 7,186,374 B2 | 3/2007 | Zelina et al. | |
| 7,393,373 B1 | 7/2008 | Krippner et al. | |
| 2002/0159915 A1 * | 10/2002 | Zelina et al. | 422/3 |
| 2003/0230567 A1 * | 12/2003 | Centanni et al. | 219/628 |
| 2006/0185321 A1 | 8/2006 | Raynaud | |
| 2010/0089009 A1 | 4/2010 | Till | |
| 2010/0166602 A1 * | 7/2010 | Bacik | 422/28 |
| 2011/0133369 A1 | 6/2011 | Martini et al. | |

FOREIGN PATENT DOCUMENTS

| | | |
|---|---|---|
| DE | 19919623 | 2/2000 |
| DE | 69520445 | 9/2001 |
| DE | 102007017938 | 10/2008 |
| DE | 102008038141 | 2/2010 |
| WO | WO2010020529 | 2/2010 |

OTHER PUBLICATIONS

European Search Report (no translation) issued in related application No. 11166850.5, dated Apr. 8, 2014 (15 pgs).

* cited by examiner

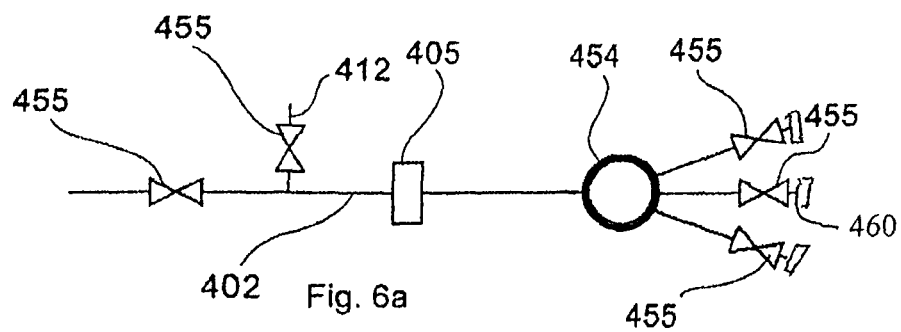
Fig. 6a
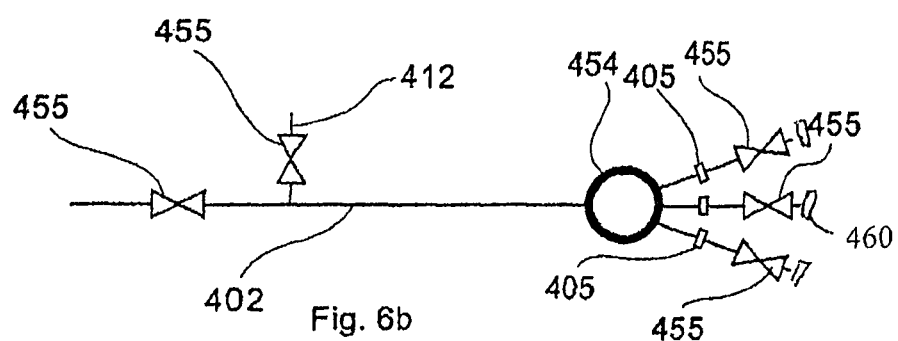
Fig. 6b
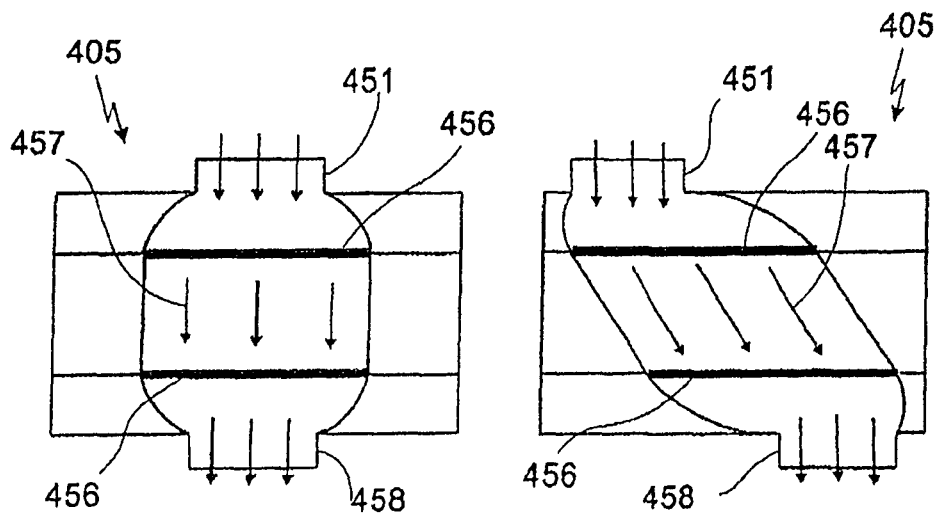
Fig. 7a
Prior Art
Fig. 7b

APPARATUS AND METHOD OF CLEANING GAS IN BLOW MOULDING MACHINES

FIELD OF THE INVENTION

The invention relates to an apparatus and a method of cleaning gas in blow moulding machines for shaping plastics material pre-forms to form plastics material containers.

BACKGROUND OF THE INVENTION

Blow moulding machines for shaping plastics material pre-forms to form plastics material containers have long been known from the prior art. It is customary for apparatus of this type to have a plurality of blow moulds which in each case form a cavity, inside which the plastics material pre-forms are capable of being shaped to form containers, inside which pre-forms of plastics material (plastics material pre-forms) are expanded to form plastics material containers. In order to expand the plastics material pre-forms, the apparatus has a pressure-stressing device which acts upon the plastics material pre-forms with a medium such as for example compressed air. As a result, the plastics material pre-form is stretched both radially and in the longitudinal direction and is pressed against an inner wall of the blow mould bounding the cavity. In order to support the stretching in the longitudinal direction of the plastics material container, blow moulding machines usually have a stretch rod. Further plants for treating the containers, such as for example disinfecting devices, filling plants, closing means and the like, are usually present downstream with respect to these blow moulding devices.

For the sake of a better use of the gas over-pressure by which the plastics material pre-forms are expanded in the blow moulds to form plastics material containers, it is provided in some blow moulding machines that the over-pressure still present in the moulded plastics material container is not allowed to escape in an uncontrolled manner but is fed back and the gas is used again. This can be particularly advantageous for example if the plastics material pre-forms are first of all acted upon at a lower gas pressure in a blow moulding machine in order to carry out a preliminary stretching (possibly in parallel with the stretching of the plastics material pre-form by means of a stretch rod). This lower gas pressure can be for example the waste gas pressure from the final stretching process of other plastics material containers. In this way, it is possible to use the over pressure remaining in the stretched containers and thus to increase the efficiency of the blow moulding machine. On account of a recycling of blowing air inside the machine in this way it is possible for stretching air or preliminary blowing air no longer to have to be supplied from the outside.

In particular, in the case of modern blow moulding machines with very high throughput performance, the use of the gas pressure remaining in the plastics material containers is reasonable and economically advantageous. On account of the possibility of reducing the pumping power for producing the over-pressure, the operating costs can be lowered and emissions can be reduced. In this way it is possible for the air recovered by recycling processes of this type to be collected in an annular duct and to be used again for blowing the following containers.

Conveying the media back in order to act upon the plastics material pre-forms with pressure carries the risk, however, that impurities for example from the pre-forms may be taken along with the medium and thus that a plurality of blow moulds may be contaminated. This is critical in particular in the case of blow moulding machines with an increased hygiene level and in this case is particularly hazardous with respect to microbiological impurities, since in this way possibly harmful micro-organisms up to pathogens can penetrate into a large number of plastics material containers and thus even into the product which is filled into the moulded plastics material containers.

Accordingly, the object of the present invention is to provide a gas preparation device which makes it possible to clean the gas flows—in particular passing between a reservoir and a blow mould—in a blow moulding machine. In particular, microbiological impurities and residues of disinfecting/sterilizing agents should be removed or at least a portion of them should be significantly reduced. In addition, an object of the present invention is to make available a method of cleaning the gas flows passing between a reservoir and at least one blow mould in a blow moulding machine.

SUMMARY OF THE INVENTION

This object is attained according to the invention by an apparatus for cleaning gas in blow moulding machines for shaping plastics material pre-forms to form plastics material containers, in which at least one gas-processing device, which is capable of filtering the gas in a sterile manner and/or of reducing a quantity of an oxidative disinfecting/sterilizing agent contained in the gas flowing through and/or flowing past, is arranged in at least one gas line which is a gas supply line or a gas removal line of a blowing station. Reference is made to the fact that in the following the terms "disinfecting agent" and "sterilizing agent" can also be used synonymously.

By means of an apparatus of this type it is possible for impurities in the compressed gas supply system to be reduced and for microbial impurities possibly to be prevented completely. At least in the case of a return line of the used gas and the re-use thereof the distribution of impurities to a multiplicity of plastics material containers shaped in the blow moulding machine is prevented.

Because of its suitability and its easy availability, air in particular is suitable as a gaseous medium for use in blow moulding machines. In special cases, however, other gases can also be advantageous and use can be made of them. In this way, for example, sterile gases such as sterile air, non-flammable gases such as nitrogen or, depending upon the field of application, other gaseous media, such as for example sterilizing media, can also be used for the expansion of the containers.

In this case the gas-processing apparatus can be arranged in the form of a filter, in particular a sterile filter, both in a compressed gas line which leads to a blow mould and in a compressed gas line which leads away from a blow mould. The arrangement in a compressed gas discharge line is particularly advantageous if the latter leads to a compressed gas reservoir and so recycling of the gas can be carried out. A sterile filter in the compressed gas line leading to a blow mould filters in a sterile manner the compressed gas supplied to the blow mould and prevents micro-organisms possibly present in the compressed gas or in the compressed gas reservoir from being introduced into the plastics material container to be produced. Since, however, even the plastics material pre-forms introduced into the blow moulding machine can be soiled and contaminated microbially, it is advisable for a sterile filter also to be provided in the line leading from the blow mould to a compressed gas reservoir in order to prevent impurities from spreading into the compressed gas reservoir (through the plastics material pre-form) during the relaxation. In this case, dust and fine dust for example are also particularly important as well as microbial impurities, since they can be swirled up by the gas movements occurring in the plastics material container during the blowing process and can thus penetrate into the compressed-gas flow. Impurities of this type can likewise be separated by a suitable filter, as a result of which an accumulation in the compressed gas reservoir is avoided.

In order to prevent microbial contamination of the plastics material containers it is possible for them to be disinfected or sterilized by suitable processes. The disinfecting/sterilizing agents used are frequently oxidative disinfecting/sterilizing agents. In particular, use is made of peroxides, in which case in particular hydrogen peroxide ($H_2O_2$) is used particularly frequently on account of its pronounced microbiocidal action, environmental compatibility and its simple technical conversion ability. If possible, however, peroxides should be prevented from accumulating in an uncontrolled manner, since they can act as fire accelerator as a rule and in extreme cases can even be explosive. Hydrogen peroxide also has the tendency, particularly in the presence of metal ions, to decomposition, during which large quantities of energy are released. It is therefore important for the compressed gas to be released from residues of these oxidative disinfecting/sterilizing agents. As a result, entrainment of the oxidative disinfecting/sterilizing agents into plastics material pre-forms to be shaped and a possible accumulation in the latter is also prevented. A further possible form of a gas processing device is therefore a design in the form of a catalyst which can optionally also be used in addition to a filter device. A catalyst of this type reduces the quantity of oxidative disinfecting/sterilizing agents in the compressed gas. Hydrogen peroxide can be broken down to form water and oxygen for example in a catalyst of this type. Even before being passed through the filter, the portion of oxidative reagents is sharply reduced by a compressed gas processing downstream of a filter by means of a catalyst, so that the service life of the filter can be prolonged. A combination of a sterile filter and a catalyst is thus also advantageous depending upon the field of application.

In a preferred embodiment of the apparatus the at least one gas processing device is a filter which is capable of filtering gas in a sterile manner and this filter is arranged in a gas line through which compressed gas is capable of being supplied to a blowing station. As a result of an embodiment of this type it is possible to filter the compressed gas which is supplied to the respective blowing station. Contamination possibly already contained in the compressed gas can thus be held back. In this way, the introduction of impurities into the container shaped in the respective blow mould from the plastics material pre-form to form the plastics material container is also prevented. It is thus possible for the interval times between individual disinfection cycles of the individual blow moulds to be prolonged, and this results in a higher overall performance of the blow moulding machine.

In a further preferred embodiment of the apparatus, the at least one gas processing device is a filter which is capable of filtering gas in a sterile manner and this filter is arranged in a gas line through which compressed gas is capable of being removed from a blowing station. An embodiment of this type is used in particular to prevent contamination of the compressed gas reservoir. In the case of recycling the compressed gas, in the absence of a sterile filter of this type there is the risk that impurities, such as for example micro-organisms which are possibly present in an individual one of the plastics material pre-forms supplied to the blow moulding machine, may spread by way of the compressed gas recycling system into a multiplicity of plastics material containers. It is therefore advantageous for the compressed gas which is supplied from the blow moulds to the compressed gas reservoir to be filtered in a sterile manner beforehand. In this way, an accumulation and a possible multiplying of the microbial contamination in the compressed gas reservoir are avoided.

In a further preferred embodiment of the apparatus at least one gas processing device is a catalyst which is suitable for reducing oxidative disinfecting/sterilizing agents contained in the gas flowing through and/or flowing past in their quantity and this catalyst is arranged in a gas line through which gas is capable of being removed from a blowing station. On account of the arrangement of a catalyst in the gas line, by means of which gas is removed from the respective blow mould, the quantity of oxidative disinfecting/sterilizing agents can be significantly reduced. Disinfecting/sterilizing agents either can be introduced by way of remaining residues into possibly sterilized plastics material pre-forms or can be the consequence of a sterilization of the respective blow moulds. On account of the high oxidation potential and the energy of decomposition it is necessary to render oxidative disinfecting/sterilizing agents of this type harmless in order to prevent an uncontrolled accumulation. An accumulation of this type can lead in an extreme case to an explosion. Even without an explosion, however, the oxidative disinfecting/sterilizing agents generally used carry the risk of their fire accelerating property. It is thus absolutely necessary to avoid an uncontrolled accumulation.

Since an oxidative disinfecting/sterilizing agent which is used particularly frequently is hydrogen peroxide ($H_2O_2$), in a preferred embodiment of the apparatus the at least one catalyst is a catalyst which is suitable for reducing the quantity of $H_2O_2$ in the gas. The considerable bactericidal effect of $H_2O_2$, the environmental compatibility thereof and the simple possibility of the technical implementation of a disinfection/sterilization with $H_2O_2$ make it a preferred oxidative disinfecting/sterilizing agent. As a result of several different catalysts, $H_2O_2$ can be converted into water ($H_2O$) and oxygen ($O_2$) and can thus be rendered harmless. It would also be possible for a plurality of catalysts which are arranged in series to be used in order to remove a plurality of oxidative components from the air flow or to reduce them in this way.

Various catalysts are suitable for converting oxidative disinfecting/sterilizing agents. In a particular embodiment of the apparatus the at least one catalyst comprises a metal which is preferably selected from a group which consists of platinum (for example in the form of a platinum fabric), palladium, nickel, gold, silver, copper, rhodium, cobalt, osmium, iron, chromium, vanadium zirconium, hafnium, cerium, samarium, zinc, manganese and combinations thereof and the like. As well as the catalysts which are used particularly frequently and which contain platinum or metals of the platinum group, manganese-containing catalysts are possible. In this way for example, manganese dioxide ($MnO_2$) is known as an efficient and inexpensive catalyst for cleaning $H_2O_2$ into water ($H_2O$) and oxygen ($O_2$).

In the case of a further advantageous embodiment the apparatus has a silencer, in particular for emerging process air and this silencer preferably has a catalyst. In a further preferred embodiment it is therefore preferable for at least one of the catalysts to be combined with a silencer and/or to be integrated in a silencer. Such a combination of a catalyst and a silencer is particularly advantageous since both elements should have as large an internal surface as possible in order to make available a large contact face with the catalyst material for the disinfecting/sterilizing agents to be separated on the one hand and to provide a multiplicity of reflective faces for the sound on the other hand. It is preferable for the catalyst material to be applied as a layer (thin if possible) to a porous matrix material. As a result of the porosity both a large surface for the reaction with the residues of the disinfecting/sterilizing agents is produced and the sound is reduced. A series arrangement of the catalyst and the silencer, in which the catalyst and the silencer are designed in the form of separate elements, is therefore not necessary. This leads to a more compact design being possible.

In an embodiment the interior of a silencer can be coated with a catalyst material or catalyst material can be additionally introduced into the silencer. The sound-proofing properties can be reinforced by a special shaping of the interior of the silencer. Crooked surfaces are particularly preferred, and, in a particularly preferred manner, irregular surfaces. It is also possible, however, for the catalyst material already to have sound-proofing properties and/or to act as a sound-proofing material. This can be achieved for example by the catalyst being used in the form of a granulate, a sponge, a net or other forms with a large specific surface. In this way, sound waves can penetrate for example into the pores of the catalyst sponge or into the interspaces between particles of granulate, where they are continuously reflected between the respective surfaces, until the intensity is sharply reduced and the sound wave dies out or is strongly reduced. In this case large regions of the silencer, such as for example the walls, or a filler material consist of the catalyst material.

It is also possible for the sound-proofing material already to have a very large inner surface and merely to be coated with the catalyst material, for example subsequently. This can be carried out for example by vapour deposition, electrolytic deposition or another type of deposition. Accordingly, it is possible both for the catalyst material to be introduced directly into the silencer (for example in the form of a granulate) or for the sound-proofing properties to be produced directly by the catalyst material, and for the catalyst material to be applied as a catalytically active layer to the sound-proofing material.

Filters for sterile filtering are generally known and are commercially available with various pore sizes. Despite a high throughput performance, however, particularly small pore sizes are possible for filtering microbial impurities from gases. In a particularly preferred embodiment of the apparatus, therefore, the at least one filter for the sterile filtering of gas has pore sizes of less than 50 µm, preferably of less than 5 µm, and in a particularly preferred manner of less than 0.5 µm. On account of these small pore sizes it is possible for microbial impurities to be efficiently filtered out of the gas flowing through the filter. At the same time, however, a sufficiently large through-flow volume through the filter is additionally possible.

These sterile filters and, in particular, the filter membrane preferably consist of a material which is compatible with the disinfecting/sterilizing agent used in particular for the disinfection/sterilization of the plastics material pre-forms or the plastics material containers and which is preferably not attacked by it. Accordingly, only materials which are resistant to the disinfecting/sterilizing agent are used in the sterile filter. An undesired chemical reaction of the disinfecting/sterilizing agent with the sterile filter and, in particular, the filter membrane is thus not possible. This permits the disinfection/sterilization of the sterile filters with the respective disinfecting/sterilizing agent, and this can significantly reduce the service life of the plant. The filters need not be dismantled in order to clean them, but they can be disinfected jointly with the line system. In addition, this permits the use of these sterile filters at many different positions inside the line system for the gases used during the (stretch) blow moulding process. In this way, for example a central sterile filter can be arranged in the supply line upstream of an annular duct. This requires filters which are designed for a high volumetric flow rate. The whole of the compressed gas required for the (stretch) blow moulding processes in the possibly very many (stretch) blow moulding devices passes this filter and is cleaned by it.

In a further embodiment it is provided that at least one of the filters which are inert with respect to the disinfecting/sterilizing agent is incorporated in each case in a line which leads directly to one of the many (stretch) blow moulding devices. It is preferable for these lines to lead from a distribution system, such as for example an annular duct, to the respective (stretch) blow moulding device. As a result of this arrangement the quantity of gas passed through each individual filter is significantly reduced and the cleaning or disinfection intervals can be lengthened. In addition, with this embodiment it is possible for the respective sterile filters to be made smaller, as a result of which a reduction in costs can be achieved. In the event of a defect of one of the filters the latter can be replaced at a comparatively low cost.

In order to be able to make the filters as compact as possible at the same time as having the pre-set cleaning performance, an optimum distribution of the flow ratios over the filter face is advantageous. In particular, in the case of an arrangement in the direct gas supply line to a (stretch) blow moulding device the space available is limited, so that compact designs for the filters are preferred. In order to achieve a satisfactory cleaning performance in this case it is proposed that the gas supply and removal lines on the sterile filter should not be arranged symmetrically with respect to the longitudinal axis of the sterile filter, but offset with respect to the latter. The air supply and removal connections are accordingly set eccentrically, and this leads to an increase in the face (in particular of the membrane face) through which the air passes. This prevents laminar gas which is flowing out of the supply line into the sterile filter from contaminating the filter face more in the centre than in the edge regions. In particular, in the case of designs with a plurality of filter membranes which are likewise arranged offset in each case with respect to one another and with respect to the central axis of the sterile filter, a turbulent flow pattern of the gas flow can be caused, as a result of which the individual membranes are acted upon with gas in a substantially uniform manner. On account of this optimization of the air distribution in the sterile filter, better use can be made of the filter material, and this permits a more compact design of the sterile filter.

The supply of the disinfecting/sterilizing agent to the sterile filter can take place through the pressure medium line or through a separate line.

In order to monitor the cleaning performance, in a preferred embodiment of the apparatus a measuring appliance, which is suitable for measuring the cleaning performance of the filter or catalyst arranged upstream, is arranged in at least one of the gas lines downstream with respect to at least one filter or catalyst. As a result, the quality of the compressed gas can be constantly controlled and the interval time for necessary cleaning cycles of the filter or catalyst arranged upstream or even the entire blow moulding machine can be determined in a manner dependent upon these measurement values. The number of the cleaning or disinfection cycles can thus be reduced and the efficiency of the blow moulding machine can be increased. In addition, it is possible to determine the location of the contamination by the arrangement of a plurality of measuring appliances and, in this way, to limit the maintenance operations to special segments of the blow moulding machine. Merely the replacement of an individual gas processing device is possibly sufficient to restore a satisfactory quality of the compressed gas and the gas line systems.

It would also be possible, however, for a central measuring appliance to be arranged for example on a return flow collection container. In addition, the measuring appliance could be incorporated or fitted directly in the catalyst.

For the case in which one of the measuring appliances delivers a measurement result which indicates contamination of the respective region, it is advisable to isolate this region as quickly as possible from other regions which are not contaminated, in order to prevent further spreading of the contamination. In a particularly preferred embodiment of the apparatus a shut-off apparatus for closing the gas line is therefore arranged in at least one of the gas lines downstream with respect to at least one measuring appliance. A suitable shut-off apparatus for closing the gas line can be for example a valve which can close the contaminated line.

In order to initiate the shutting-off of a gas line in a manner dependent upon the signal of the measuring appliance, it is provided in a particularly preferred embodiment of the apparatus that the shut-off apparatus for closing the gas line is connected to at least one control device which is suitable for closing or opening the shut-off apparatus in a manner dependent upon the values determined by the measuring appliance. The control device is capable of evaluating the values determined by the measuring appliance and of drawing suitable conclusions from them on the quality of the gas and thus also on the impurities. As a result of this evaluation, control signals are sent to the shut-off apparatus which cause the latter to close the gas line in question. In the same way, the opening of the shut-off apparatus can also be carried out by the control unit even after a removal of the impurity in the portion of the line affected has possibly taken place. A manual intervention for closing the shut-off apparatus is not necessary in this automated embodiment. As a result, it is possible to react very rapidly in an automatic manner to contamination in a portion of the line and to prevent contamination of further regions of the blow moulding machine. In addition, it would be possible—in the event that sterilization of the line network is carried out by means of an oxidative agent—to protect the catalyst or other filter devices in a suitable manner by the shut-off apparatus. On account of the provision of catalysts it is possible for oxidative components, which could possibly have a negative influence upon the durability of the material or which limit a re-use of the compressed air, to be removed or rendered harmless. In the same way it is possible to prevent the oxidative components from accumulating in the recycled and re-used blowing air and—in this way—higher residual concentrations of the oxidative agent from occurring in the newly blown bottle. As a result of fitting the catalyst it is thus possible for systems for recycling blowing air to be used even in the case of previous sterilization of the pre-form.

An apparatus according to the invention is particularly advantageous if the blow moulding machine is arranged in a clean room, or if it has a clean room, inside which the containers are conveyed. In this case an apparatus as it has been described in WO 2010/020 529 A2 can be provided for example. In this way, the subject matter of this disclosure is also made by reference into the subject matter of the present disclosure in its entirety.

A further essential aspect of the invention for attaining the object set is a method of cleaning gas in blow moulding machines for shaping plastics material pre-forms to form plastics material containers, in which case the gas is conveyed through at least one gas-processing device which sterilizes the gas and/or reduces residual quantities of oxidative disinfecting/sterilizing agent in the gas by means of a catalyst. By means of this process it is possible to clean gas in the interior of a blow moulding machine. The impurity and/or contamination both of the finished plastics material containers and the (compressed) gas supply system can be prevented or at least considerably reduced by passing the compressed gas, which is required in blow moulding machines for shaping plastics material pre-forms to form plastics material containers, through suitable gas-processing devices.

BRIEF DESCRIPTION OF THE DRAWINGS

Further advantages, aims and characteristics of the present invention are explained with reference to the following description of the accompanying drawing in which an apparatus according to the invention for cleaning gas in blow moulds for shaping plastics material pre-forms into plastics material containers is illustrated by way of example. In the drawing

FIGS. 6a, 6b show different arrangements of the sterile filter or filters in the line system, and FIGS. 7a, 7b show different embodiments of the sterile filters.

DETAILED DESCRIPTION OF THE INVENTION

Figure 1:
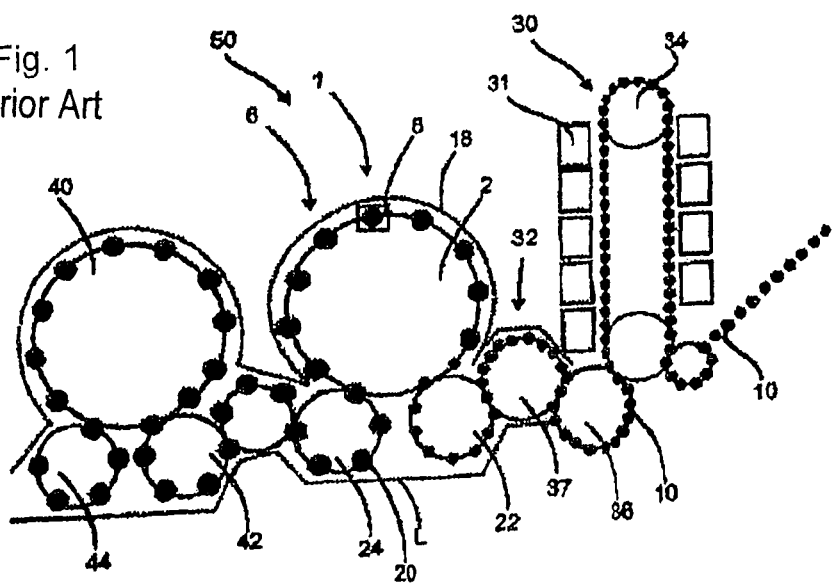
FIG. 1 is a diagrammatic illustration of a system for producing plastics material containers according to the prior art.

FIG. 1 is a diagrammatic illustration of a plant according to the prior art for producing plastics material containers. This plant 50 has a heating device 30 in which plastics material pre-forms 10 are heated. In this case these plastics material pre-forms 10 are conveyed through this heating device 30 by means of a conveying device 34, such as a circulating chain in this case, and are heated by a plurality of heating elements 31. This heating device 30 is followed by a transfer unit 36 which transfers the pre-forms 10 to a sterilization device 32. In this case this sterilization device 32 likewise has a conveying wheel 37, and sterilization elements can be arranged on this conveying wheel 37 or can even be arranged in a stationary manner. Sterilization by hydrogen peroxide gas or even, as mentioned above, by electromagnetic radiation, is possible for example in this region. In particular, an internal sterilization of the pre-forms is carried out in this region.

The reference number 6 designates in its entirety a clean room, the external boundaries of which are indicated in this case by the dotted line L. It is evident that this clean room 6 starts in the region of the sterilization unit 32. Air lock devices can be provided in this region in order to introduce the plastics material pre-forms into the clean room 6, without too much gas being lost inside the clean room during this.

As indicated by the dotted line L, the clean room is adapted to the external shape of the individual components of the plant. In this way, the volume of the clean room can be reduced.

The reference number 1 designates in its entirety a shaping device in which a plurality of blowing stations 8 are arranged on a conveying wheel 2, only one of these blowing stations 8 being illustrated in this case. The plastics material pre-forms 10 are expanded to form containers 20 by these blowing stations 8. Although it is not shown in detail in this case, the entire region of the conveying device 2 is not situated inside the clean room 6, but the clean room 6 or isolator is designed as it were in the form of a mini-isolator inside the apparatus as a whole. In this way it would be possible for the clean room to be designed in the manner of a duct at least in the region of the shaping device 1.

The reference number 22 relates to a supply device which transfers the pre-forms to the shaping device 1, and the reference number 24 relates to a removal device which removes the produced plastics material containers 20 from the shaping device 1. It is evident that in the region of the supply device 22 and the removal device 24 the clean room 6 has recesses in each case which receive these devices 22, 24. In this way, a transfer of the plastics material pre-forms 10 to the shaping device 1 or a taking-up of the plastics material containers 20 from the shaping device 1 can be achieved in a particularly advantageous manner.

The expanded plastics material containers are transferred by a transfer unit 42 to a filling device 40 and are then removed from this filling device 40 by way of a further conveying unit 44. In this case the filling device 40 is also situated inside the aforesaid clean room 6. In addition, in the case of the filling device it would also be possible for the entire filling device 40 with for example a reservoir for a beverage not to be arranged completely inside the clean room 6, but in this case too only those regions in which the containers are actually conveyed. In this respect the filling device could also be designed in a similar manner to the apparatus 1 for shaping plastics material pre-forms 10.

As mentioned, in the region of the apparatus 1 the clean room 6 is reduced to as small a region as possible, i.e. essentially to the blowing stations 8 themselves. As a result of this small design of the clean room 6 a clean room can be produced more easily and more rapidly in any case, and, in addition, keeping things sterile in the operating phase is less complicated. Less sterile air is also required, and this leads to smaller filtering plants and the risk of uncontrolled swirl formation is also reduced.

Figure 2:
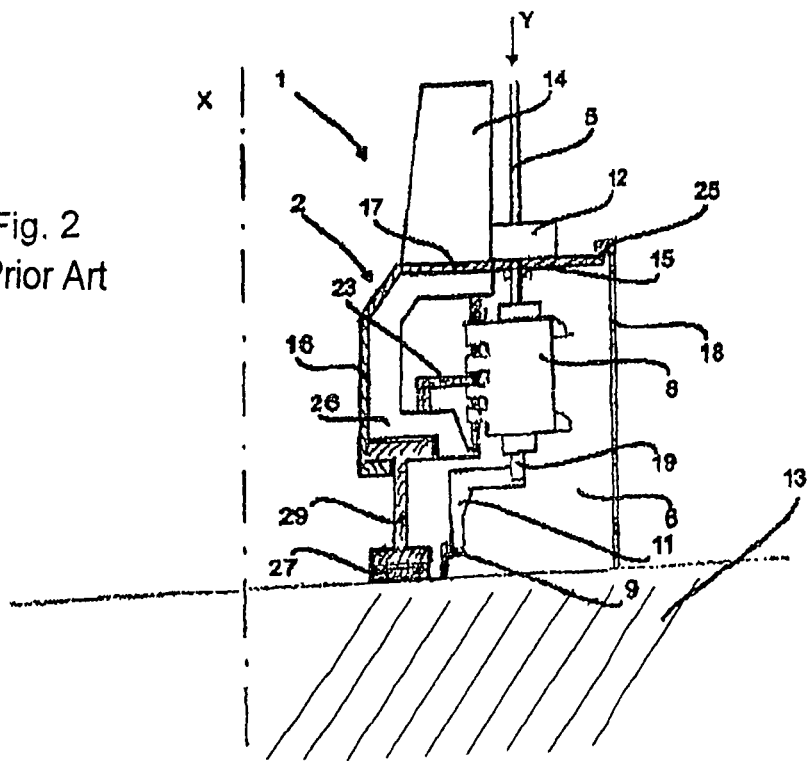
FIG. 2 is a view of a clean room in the region of a blowing station according to the prior art.

FIG. 2 is a detailed illustration of the apparatus 1 in the region of a blowing station 8. A plurality of blowing stations 8 of this type are moved so as to rotate about an axis X by a conveying device 2. As is evident from FIG. 2, the blowing station 8 is guided inside the clean room 6, which in this case is designed in the manner of a duct. This clean room 6 is closed off by a movable lateral wall 16 and a cover 17 formed in one piece with this lateral wall 16. In this case this lateral wall 16 and the cover 17 rotate jointly with the blowing station 8.

The reference number 18 relates to a further wall which bounds the clean room 16. In this case this wall 18 is a wall which is situated on the outside and which is arranged so as to be stationary. A sealing device 25, which seals off the mutually movable elements 17 and 18 from each other, for example—as mentioned above—with the use of a water seal, is provided between the cover 17 and the wall 18. The lower region of the wall 18 is arranged on a base 13 in a fixed and sealed manner. A support 26, which likewise moves in a rotating manner and on which a holding device 23 holding the blowing station 8 is arranged in turn, is provided inside the clean room 6 and, in this case, resting directly against the wall 16.

The reference number 11 relates to a follower device which can be actuated by a guide cam 9 in order to open and close the blowing station on its path through the clean room 6, in order, in particular, to insert the plastics material pre-form in the blowing station and in order also to remove it again. In this case a guide cam 9 is also arranged inside the clean room 6. It would also, however, be possible for example for a portion 19 below the individual blowing stations 8 to be brought out of the clean room 6 beforehand.

The conveying device 2 can have still further elements which are arranged upstream the clean room 6.

In this case the support 26 is arranged on a holding member 29 in a fixed manner and this holding member in turn is movable with respect to the base 13. In this case the reference number 27 relates to a further sealing device which in this region too produces a sealing of the regions 13 and 29 movable with respect to each other.

The reference number 5 relates to a stretch rod which is movable with respect to the blowing station in order to stretch the plastics material pre-forms 10 in the longitudinal direction thereof. In this case a slide 12, with respect to which the stretch rod is movable in the Y direction, is arranged on the cover 17. The reference number 14 relates to a further holding means for this slide 12 of the stretch rod 5.

It is evident that during the blowing procedure specific regions of the stretch rod are both outside the clean room 6 and inside the clean room. For this purpose it is possible for a protection device, such as a folding bellows, which surrounds the stretch rod 5, to be provided outside the clean room 6 or above the slide 12, so that no region of the stretch rod 5 comes directly into contact with the outside environment.

The above-mentioned heating device for heating the plastics material pre-forms is preferably likewise designed to be aseptic. This means that the plastics material pre-forms already in the region of the heating device 30, in contrast to what is shown in FIG. 1, can be conveyed through a clean room and this clean room extends for example in a continuous manner by way of the blow moulding machine as far as the filling means. In this case it is possible for example for the entire heating device 30 to be arranged inside a sterile room, but it would also be possible, however, in particular, for the region in which the plastics material pre-forms are conveyed to be enclosed in this case too in the form of a sterile room with respect to the environment. In this way it would be possible, for example, for the plastics material pre-forms to be conveyed by means of mandrels which engage in their opening and during this the mandrels project through a wall into a clean room. This clean room could likewise be acted upon with an over-pressure, so that no air from the environment can penetrate into this clean room.

In this case the heating device could be designed in the form of an infrared heating device, as illustrated in FIG. 1. It is advantageous, however, for a microwave heating device to be used as the heating device in this case. Microwave heating devices of this type for heating plastics material pre-forms are known per se from the prior art. In this case a plurality of microwave heating stations could be arranged for example on a support wheel. The plastics material pre-forms could be supplied to these individual heating stations by way of switches. On account of the design with individual heating stations a microwave-based heating device is particularly suitable for a combination with sterile rooms.

Figure 3:
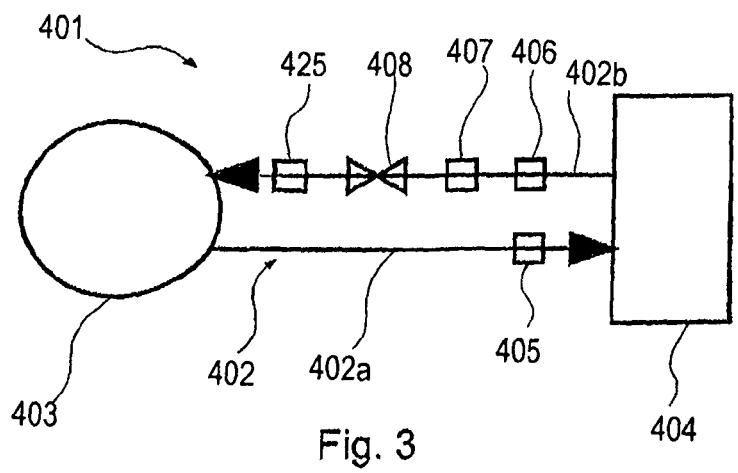
FIG. 3 is a diagrammatic illustration of an apparatus with connecting lines between a reservoir and an individual blowing station.

FIG. 3 is a diagrammatic illustration of an apparatus 401 with connecting lines 402, 402a, 402b between a reservoir 403 and an individual blowing station 8. In this case the lower arrow designates a gas supply line 402a through which gas at a pre-set pressure $p_n$ can be conveyed from a reservoir 403 to a blowing station 8. In order to prevent impurities in the blowing station 8, a sterile filter 405 is arranged in this gas supply line 402a. Any microbial impurities possibly present are kept back by this sterile filter 405 before they can come into contact with the plastics material pre-forms or the plastics material containers. A catalyst 406 is arranged in a gas removal line 402b which is indicated by the upper arrow.

In the event of a necessary disinfection of the blow mould or the blowing station 8, it is possible for oxidative disinfecting/sterilizing agent possibly remaining in the blowing station 8 to be rendered harmless with this catalyst 406. In the case of $H_2O_2$ as a disinfecting/sterilizing agent, a clearage takes place into water ($H_2O$) and oxygen ($O_2$). A measuring appliance 407, which checks the quality of the gas flowing through, is arranged downstream with respect to the catalyst 406. A shut-off apparatus 408, which is arranged further downstream and which can close the gas line 402b, can be controlled with respect to the quality of the gas in a manner dependent upon the measurement values obtained. As a result, if the gas is fed back from a blowing station 8 into the reservoir 403, an accumulation of the oxidative disinfecting/sterilizing agent inside the lines or inside the reservoir 403 is prevented.

In order to prevent microbial contamination of the reservoir 403 as well, a further sterile filter 425 is arranged in the line system 402 in the embodiment shown. In order to prevent microbial contamination of the reservoir 403, the gas conveyed back into the reservoir 403 is filtered in a sterile manner before entry into the reservoir 403. Impurities, which are introduced in a plastics material pre-form for example into the blow moulding machine, can thus be kept back from entering the compressed gas circuit.

Figure 4:
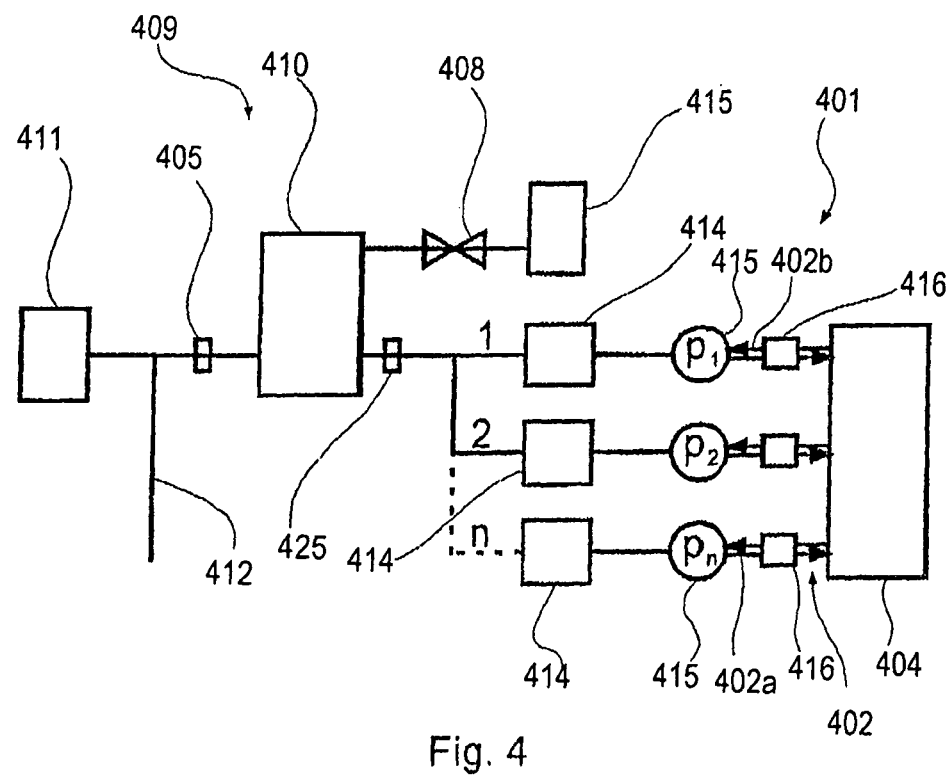
FIG. 4 is a diagrammatic illustration of a system of lines with different gas pressures inside a blow moulding machine.

FIG. 4 is a diagrammatic illustration of a system of lines 409 with different gas pressures $p_n$ inside a blow moulding machine. In the system 409 shown, a gas distributor 410 is fed with compressed gas from a central compressed gas production unit (not shown) by means of a compressed gas supply line 411. The supply of the compressed gas is already carried out in a sterile manner and this is provided for by the feed of a sterilization gas 412 as well as a sterile filtering by means of a filter 405. Starting from the gas distributor 410, both the gas consumer means 413 without direct contact with the product or packaging material and pressure reducers 414 for supplying the blowing stations 8 are supplied with compressed gas. The line to the gas consumer means 413 without direct contact with the product or packaging material is regulated by way of a shut-off apparatus 408 such as for example a valve. The supply to the pressure reducers 414 is carried out once again through a sterile filter 425. Various compressed gas reservoirs 415 such as for example annular ducts, which in turn are in contact with the individual blowing stations 8, are arranged downstream of the pressure reducers 414. In this case the individual reservoirs 415 have gas pressures $p_n$ which can be both the same or different from one another. The connection 402 between the individual reservoirs 403 and the individual blowing stations 8 can be carried out in a manner similar to the embodiment shown in FIG. 1. It is also possible, however, in a manner deviating from the example shown, for the gas fed back from the blowing station 8 to be supplied not to that reservoir 415 from which it was supplied to the blowing station 8, but to a different reservoir 415 which is holding gas at a lower pressure ready. By way of example, the waste gas from a process step which was carried out at the highest pressure $p_1$ can be supplied at the pressure $p_2$ to the reservoir 415. An interlinking of the various reservoirs 403 in this way, however, increases the risk of contamination of large regions of the blow moulding machine, and so it is advantageous for suitable safety measures to be provided. The gas processing devices 416 shown in the diagrammatic drawing illustrated can therefore be arranged both in the gas supply line 402a and in the gas removal line 402b.

Figure 5A:
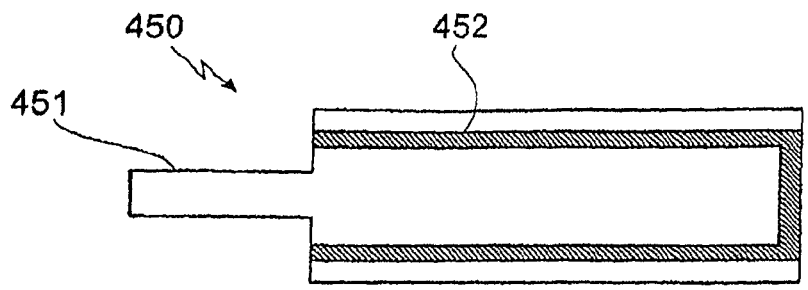
FIGS. 5a-5c show different variants of embodiment of a silencer with an integrated catalyst.
Figure 5B:
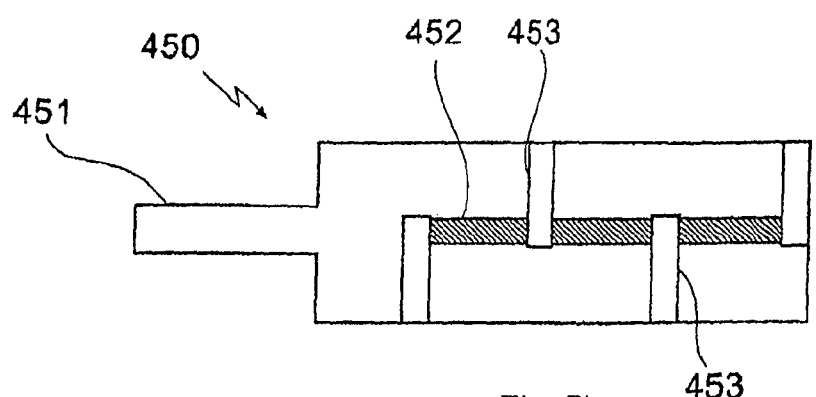
Figure 5C:
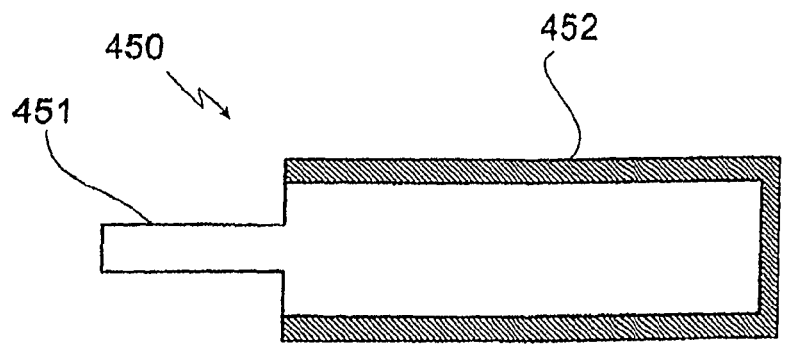

Different variants of embodiment of a silencer 450 with an integrated catalyst are shown in FIGS. 5a-5c. In all the variants of embodiment shown by way of example a supply line or a connecting line respectively, by way of which gas can be introduced into the silencer 450, is shown in the left-hand region. An embodiment, in which the catalyst layer 452 has been applied to the inside of the silencer 450, is shown diagrammatically in FIG. 5a. It is possible to fall back upon elements known from the prior art for the catalyst-carrying layer. By way of example, porous sintered moulded parts or ceramics can act as a base to which the catalyst is applied. The outer layer consists of a sound-proofing material, for example of polypropylene or the like. Waste gases from the silencer can be either discharged into the environment by way of the outer face or removed by way of a separate waste gas line.

FIG. 5b shows a variant of a silencer 450 with an integrated catalyst in which the gas flow in the interior of the silencer 450 is deflected by way of walls 453 in different portions in each case. As a result, the gas flow is guided multiple times through a catalyst layer 452 when passing through the silencer. The catalyst layers are arranged in intermediate spaces. Other arrangements of the walls 453 and the catalysts 452 are also possible. For example, the catalyst 452 permeable to gas could be arranged as an extension of the walls 453 impermeable to gas in each case. The number of the walls 453 can be adapted to the respective requirements and is usually between 1 and 100, preferably between 2 and 20. In a silencer of this type the background noise and the through-flow quantity can be influenced by precisely defined cross-sections and shapes.

A variant of a silencer 450 with an integrated catalyst is shown in FIG. 5c, in which the catalyst material 452 is built up in such a way that it also has sound-proofing properties at the same time. For example, it can be built up in the manner of a sponge, in the form of a multi-ply layer of narrow-mesh nets or in other similar arrangements with a large inner surface and therefore many sound-reflecting faces. The sound-proofing material is replaced by a material which is sound-proofing and at the same time catalytic. The catalyst can be produced in the form of a granulate, thin layer on a porous material or in a sintered form or in other forms directly of a catalytic material. When the sound passes through this layer, it is reflected multiple times in different directions and the sound waves die out. At the same time disinfecting/sterilizing agent conveyed with the gas flow also comes into contact with the catalyst 452 and can be cleared.

FIG. 6a shows a variant of the possible different arrangements of the sterile filter or filters 405 in the line system. In the variant illustrated in FIG. 6a a central sterile filter 405 is arranged in the line system 402. The latter is preferably situated in a position downstream of the feed of the sterilization gas 412, but upstream of the annular duct 454. The individual gas flows to blowing station 460 can be regulated by way of various valves 455. A rotary distributor preferably likewise arranged downstream of the feed of the sterilization gas 412 is not shown in FIGS. 6a and 6b.

A further possible arrangement of sterile filters 405 in the line system 402 is shown in FIG. 6b. In this example a plurality of sterile filters 405 are arranged downstream of the feed of the sterilization gas 412, but in contrast to the embodiment shown in FIG. 6a also downstream of the annular duct 454 and upstream with respect to the respective blowing stations 460. Valves 455, which regulate the gas supply to the individual blowing stations, are arranged downstream of the sterile filters 405.

FIG. 7a shows a sterile filter 405 according to the prior art. The filter membranes 456 are arranged directly one behind the other in the flow direction of the gas 457. The centre of each membrane is situated on one axis with the centres of the gas supply line 451 and the gas removal line 458. A drawback of this design is that in the case of a predominantly laminar flow pattern the flow velocity of the gas in the centre is greater than in edge regions, as a result of which a greater contamination of the centre of each of the membranes can occur. In addition, the edge regions of the membranes are acted upon with smaller quantities of disinfecting/sterilizing agent, since the gas flow is less here. This can lead to insufficient sterilization taking place there. If it is nevertheless necessary to provide this, large quantities of disinfecting/sterilizing agent are required.

In the variant of a sterile filter 405 shown in FIG. 7*b* the filter membranes 456 are offset with respect to one another transversely to the longitudinal direction (or the flow direction of the gas) of the sterile filter 405 in the flow direction of the gas 457. In addition, the connections for the supplied and removed air are positioned eccentrically. As a result, the gas is forcibly deflected, as a result of which a turbulent flow pattern can be produced. As a result, a more uniform distribution of the flow velocities can be achieved over the entire membrane face. This results in a more uniform deposition of impurities on the respective filter membrane 456 on the one hand, and also in a more homogeneous distribution of disinfecting/sterilizing agent over the entire filter membrane 456 on the other hand. In addition, this leads to an enlargement of the (membrane) face through which the air passes. Better use can be made of the filter material by optimization of the air distribution in the membrane filter. In this way, even in the case of a smaller use of disinfecting/sterilizing agent it is possible for the edge regions of filter membranes 456 to be adequately disinfected or sterilized.

In summary, the apparatus according to the invention and the method according to the invention create the possibility of filtering, in particular, recovered compressed air in a sterile manner again before renewed use and therefore of maintaining the sterility of the entire system at each moment in time during the production.

The Applicants reserve the right to claim all the features disclosed in the application documents as being essential to the invention, insofar as they are novel either individually or in combination as compared with the prior art.

LIST OF REFERENCES 1 shaping apparatus
2 conveying wheel
5 stretch rod
6 clean room
8 blowing station
10 plastics material pre-forms, container
11 follower device
12 slide
13 base
14 holding means
15 bend
16 lateral wall
17 cover
18 wall
19 portion
20 plastics material container
22 supply device
23 holding device
24 removal device
25 sealing device
26 support
27 sealing device
29 holding member
30 heating device
31 heating elements
32 sterilization device
34 conveying device
36 transfer unit
37 conveying wheel
40 filling device
42 transfer unit
44 conveying unit
50 plant/system
401 apparatus
402 gas line
402*a* gas supply line
402*b* gas removal line
403 reservoir
405 sterile filter
406 catalyst
407 measuring appliance
408 shut-off apparatus
409 system of lines
410 gas distributor
411 compressed gas production unit
412 sterilization gas supply line
413 gas consumer means without direct contact with the product or packaging material
414 pressure reducer
415 compressed gas reservoir with gas pressure $p_n$
416 gas processing device
425 sterile filter
450 silencer with catalyst
451 supply line—connection apparatus
452 catalyst layer
453 wall
454 annular duct
455 valve
456 filter membrane
457 flow direction
458 removal line—connection apparatus
$p_n$ gas pressure
L line

The invention claimed is:

1. A method of cleaning and/or sterilizing gas in blow moulding machine having a blowing station, said blow moulding machine comprising a compressed gas supply system for shaping plastics material pre-forms to form plastics material containers, wherein compressed gas supplied via an annular-shaped distribution duct from a plurality of separate gas reservoirs at the same or different gas pressures is conveyed through at least one gas-processing device which sterilizes the compressed gas using a sterile filter having a pore size of less than 50 µm and optionally reduces residual quantities of oxidative disinfecting/sterilizing agent in the compressed gas by reaction with a catalyst, wherein the sterile filter is arranged in a line system of the blow moulding machine and is cleaned by the oxidative disinfecting/sterilizing agent which is also used for the disinfection/sterilization of the plastics material pre-forms and/or the plastics material containers, wherein the compressed gas is introduced first through the sterile filter, then through the annular-shaped distribution duct and then to the blowing station, and, employing said compressed gas to blow plastics material pre-forms to plastics material containers, and wherein the sterile filter is a central sterile filter and is situated in a position downstream of a feed of the oxidative disinfecting/sterilizing agent but upstream of the annular-shaped distribution duct.

2. A method of cleaning and/or sterilizing gas in blow moulding machine having a blowing station, said blow moulding machine comprising a compressed gas supply system for shaping plastics material pre-forms to form plastics material containers, wherein compressed gas supplied via an annular-shaped distribution duct from a plurality of separate gas reservoirs at the same or different gas pressures is conveyed through at least one gas-processing device which sterilizes the compressed gas using a sterile filter having a pore size of less than 50 µm and optionally reduces residual quantities of oxidative disinfecting/sterilizing agent in the compressed gas by reaction with a catalyst, wherein the sterile filter comprises a plurality of sterile filters arranged. in a line system of the blow moulding machine and is cleaned by the oxidative disinfecting/sterilizing agent which is also used for the disinfection/sterilization of the plastics material pre-forms andlor the plastics material containers, wherein the compressed gas is introduced first through the annular-shaped distribution duct, then through the a plurality of sterile filters and then to their respective blowing stations, and, employing said compressed gas to blow plastics material pre-forms to plastics material containers, and wherein the plurality of sterile filters are arranged downstream of a feed of the oxidative disinfecting/sterilizing agent and also downstream of the annular-shaped distribution duct.

3. A method of cleaning and/or sterilizing gas in blow moulding machine having a blowing station, said blow moulding machine comprising a compressed gas supply system for shaping plastics material pre-forms to form plastics material containers, wherein compressed gas is conveyed through at least one gas-processing device which sterilizes the compressed gas using a sterile filter and optionally reduces residual quantities of oxidative disinfecting/sterilizing agent in the compressed gas by reaction with a catalyst, wherein the sterile filter is arranged in a line system of the blow moulding machine and is cleaned by the oxidative disinfecting/sterilizing agent which is also used for the disinfection/sterilization of the plastics material pre-forms and/or the plastics material containers, and; employing said compressed gas to blow plastics material pre-forms to plastics material containers, wherein the method further comprises using at least one silencer, which silencer has at least one catalyst, wherein the at least one catalyst is combined with the at least one silencer and/or is integrated in the at least one silencer.

4. The method according to claim 3, wherein the at least one gas-processing device is arranged in a gas line which is a gas supply line or a gas removal line of the blowing station.

5. The method according to claim 3, wherein the compressed gas is removed from the blowing station by a gas removal line.

6. The method according to claim 3, wherein the at least one gas-processing device, in addition to the sterile filter, also includes the catalyst which is suitable for reducing oxidative disinfecting/sterilizing agents contained in the compressed gas flowing through and/or flowing past in their quantity, which catalyst is arranged in a gas line through which the compressed gas is capable of being removed from the blowing station.

7. The method according to claim 6, wherein the catalyst is suitable for reducing a quantity of $H_2O_2$ in the compressed gas.

8. The method according to claim 6, wherein the catalyst comprises a metal selected from a group consisting of platinum, palladium, nickel, gold, silver, copper, rhodium, cobalt, osmium, iron, chromium, vanadium, zirconium, hafnium, cerium, samarium, zinc, and manganese, and a combination of two or more of said metals.

9. The method according to claim 3, wherein the sterile filter for the sterile filtering of gas has pore sizes of less than 5 µm.

10. The method according to claim 9, wherein the sterile filter for the sterile filtering of gas has pore sizes of less than 0.5 µm.

11. The method according to claim 3, wherein a measuring appliance, for measuring the cleaning perfomance of the sterile filter or a catalyst arranged upstream, is arranged in at least one gas line downstream with respect to at least one of the sterile filter or catalyst.

12. The method according to claim 11, wherein a shut-off apparatus is arranged in at least one gas line downstream with respect to at least one measuring appliance.

13. The method according to claim 12, wherein the shut-off apparatus for closing the at least one gas line is connected to at least one control device which is suitable for closing or opening the shut-off apparatus in a manner dependent upon the values determined by the at least one measuring appliance.

* * * * *